United States Patent
Eicken et al.

(10) Patent No.: US 6,362,380 B1
(45) Date of Patent: Mar. 26, 2002

(54) PREPARATION OF NITROBIPHENYLS

(75) Inventors: Karl Eicken; Joachim Gebhardt, both of Wachenheim; Harald Rang, Altrip; Michael Rack, Heidelberg; Peter Schäfer, Ottersheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/645,980

(22) Filed: Jun. 1, 2000

Related U.S. Application Data

(63) Continuation of application No. 09/142,715, filed on Sep. 9, 1998, now Pat. No. 6,087,542.

(30) Foreign Application Priority Data

Mar. 13, 1996 (DE) .......................................... 19609765

(51) Int. Cl.$^7$ ............................................ C07C 205/00
(52) U.S. Cl. ...................... 568/933; 568/931; 568/928; 568/585; 568/586
(58) Field of Search ............................ 563/931, 928, 563/933, 585, 586

(56) References Cited

FOREIGN PATENT DOCUMENTS

WO         9622967     *   8/1996

OTHER PUBLICATIONS

Eiichi et al., Synthesis of biaryls via palladim–catalyzed cross coupling, Org. Synth. (1988), 66, 67–74.*

* cited by examiner

Primary Examiner—Johann Richter
Assistant Examiner—J. Parsa

(74) Attorney, Agent, or Firm—Keil & Weinkauf

(57) ABSTRACT

A process for preparing nitrobiphenyls of the formula I

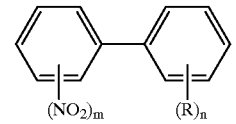

(I)

where m is 1 or 2, R is halogen R' or OR', where R' is a C-organic radical which may carry groups inert under the reaction conditions, n is 0, 1, 2 or 3, and, in the case of n being 2 or 3, the radicals R are the same or different, by reacting a chloronitrobenzene of the formula II

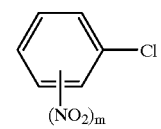

(II)

in the presence of a palladium catalyst and a base in a solvent with a phenylboronic acid (IIIa)

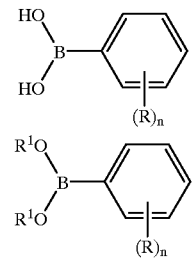

(IIIa)

(IIIb)

or an alkyl ester thereof of the formula IIIb where $R^1$ is $C_1$–$C_6$-alkyl, or an anhydride thereof.

The compounds I are useful as precursors for biphenylamines, which in turn are intermediates for fungicidal crop protection agents.

21 Claims, No Drawings

PREPARATION OF NITROBIPHENYLS

This application is a continuation of Ser. No. 09/142,715 filed Sep. 9, 1998, now U.S. Pat. No. 6,087,542.

The present invention relates to a process for preparing nitrobiphenyls of the formula I

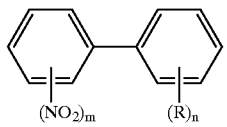

(I)

where m is 1 or 2, R is halogen, R' or OR', where R' is a C-organic radical which may carry groups inert under the reaction conditions, n is 0, 1, 2 or 3, and, in the case of n being 2 or 3, the radicals R are the same or different, which comprises reacting a chloronitrobenzene of the formula II

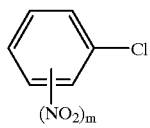

(II)

in the presence of a palladium catalyst and a base in a solvent with a phenylboronic acid (IIIa)

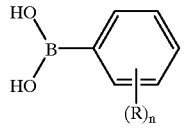

(IIIa)

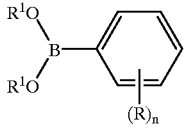

(IIIb)

or an alkyl ester thereof of the formula IIIb where $R^1$ is $C_1$–$C_6$-alkyl, or an anhydride thereof.

Synth. Commun. 11 (1981), 513, discloses that it is not possible to couple phenylboronic acid with chlorobenzene in the presence of tetrakis(triphenylphosphine)palladium and sodium ethoxide to afford biphenyl.

Tetrahedron Lett. 32 (1991), 2277, discloses that the coupling reaction between phenylboronic acid and chlorobenzene, when using the catalyst [1,4-bis(diphenylphosphine)butane]palladium(II) dichloride, results in a yield of only 28%

It is an object of the present invention to provide an economical process for preparing nitrobiphenyls by employing readily accessible palladium catalysts.

We have found that this object is achieved by the process defined at the outset.

The phenylboronic acids IIIa, esters IIIb and anhydrides such as IIIc, which hereinafter will collectively be referred to as "boron compounds III", are generally known or obtainable in a manner known per se (cf. for example Org. Synth. Coll. Vol. IV, page 68).

Preferred C-organic radicals R' are:
alkyl and alkenyl groups, in particular those having 1 to 12 carbons such as methyl, ethyl, propyl, butyl and allyl,
alkylcarbonyl and alkoxycarbonyl groups, in particular those having 1 to 6 carbons such as acetyl, methoxycarbonyl and ethoxycarbonyl,
cycloalkyl groups, in particular those having 3 to 10 carbons such as cyclopentyl, cyclohexyl and 1-methylcyclohexyl, and also
phenyl and phenoxy groups.

Substituents of the C-organic radical R' inert under the reaction conditions are preferably halogen and furthermore alkyl and alkoxy groups.

Further C-organic radicals R' are:
cyano and formyl groups (—CHO).

The anhydrides are normally products of the combination of two or more equivalents of phenylboronic acid IIIa with elimination of water, containing intermolecular B—O—B bridges. Preference is given to cyclic anhydrides of the formula IIIc.

(IIIc)

This has to be taken into consideration hereinafter with regard to the molar amounts specified for boron compounds III. These molar amounts are always based on phenylboronic acid equivalents.

In general, alkyl esters of the formula IIIb where $R^1$ is $C_1$–$C_6$-alkyl can be used. Preferred alkyl esters IIIb are the dimethyl esters and the diethyl esters.

Preferred starting materials in the process according to the invention are the phenylboronic acids IIIa.

Furthermore, preferred starting materials are boron compounds of the formula III in which R is a $C_1$–$C_4$-alkyl group or halogen and in particular methyl, fluorine or chlorine.

In addition, preferred starting materials are boron compounds III in which n is 1 and, in particular, 0.

Very particularly preferred starting compounds IIIa are 4-methyl-phenylboronic acid, 4-fluorophenylboronic acid and especially 4-chlorophenylboronic acid.

Preferred starting materials are nitrochlorobenzenes II carrying a single nitro group (m=1), in particular 4-nitrochlorobenzene and especially 2-nitrochlorobenzene.

The boron compounds III (phenylboronic acid equivalents) are normally employed in up to 50 percent excess, preferably up to 20 percent excess, and very preferably in equimolar amounts, based on the compounds II.

The bases used can be organic bases such as tertiary amines. Preference is given to using triethylamine or dimethylcyclohexylamine, for example.

Preferred bases are alkali metal hydroxides, alkaline earth metal hydroxides, alkali metal carbonates, alkaline earth metal carbonates, alkali metal bicarbonates, alkali metal acetates, alkaline earth metal acetates, alkali metal alkoxides and alkaline earth metal alkoxides, in mixtures and, in particular, on their own.

Particularly preferred bases are alkali metal hydroxides, alkaline earth metal hydroxides, alkali metal carbonates, alkaline earth metal carbonates and alkali metal bicarbonates.

Very particularly preferred bases are alkali metal hydroxides, for example sodium hydroxide and potassium hydroxide, and alkali metal carbonates and alkali metal bicarbonates, for example lithium carbonate, sodium carbonate and potassium carbonate.

In the process according to the invention, the base is preferably employed in a ratio of from 100 to 500 mol %, particularly preferably from 150 to 400 mol %, based on the boron compound III.

Suitable palladium catalysts are palladium complexes having palladium in the oxidation state zero, palladium salts in the presence of complexed ligands or metallic palladium which is, if appropriate, deposited on supports, preferably in the presence of complexed ligands.

Suitable complexed ligands are neutral ligands such as triarylphosphines which are unsubstituted or substituted in the aryl rings. The water solubility of the palladium complexes can be improved by the following substituents: sulfonic acid salt groups, sulfonic acid groups, carboxylic acid salt groups, carboxylic acid groups, phosphonic acid salt groups, phosphonic acid groups, phosphonium groups, peralkylammonium groups, hydroxyl groups and polyether groups.

Of the palladium complexes having palladium in the oxidation state 0, preference is given to using tetrakis(triphenylphosphine)palladium and to tetrakis[tri(o-tolyl)phosphine]palladium.

In the palladium salts employed in the presence of complexed ligands, the palladium is normally present in the oxidation state plus two. Preference is given to using palladium acetate or palladium chloride.

As a rule, 2 to 6 equivalents of the abovementioned ligands, in particular triphenylphosphine, are complexed with one equivalent of the palladium salt (cf. for example J. Org. Chem. 49 (1984), 5240).

Otherwise, such soluble palladium complexes are generally known (cf. for example Angew. Chem. 105 (1993), 1589).

Metallic palladium is preferably used as a powder or on a support, for example as palladium on activated carbon, palladium on aluminum oxide, palladium on barium carbonate, palladium on barium sulfate, palladium on calcium carbonate, palladium on aluminum silicates such as montmorillonite and palladium on $SiO_2$, in each case having a palladium content of 0.5 to 12% by weight. Besides palladium and the support, these catalysts may contain further, doping substances, for example lead.

When using metallic palladium which is, if appropriate, deposited on supports, the simultaneous use of the abovementioned complexed ligands is especially preferred, in particular the use of palladium on activated carbon in the presence of triphenylphosphine as complexed ligand, the phenyl groups of the triphenylphosphine preferably being substituted with a total of one to three sulfonate groups.

As a rule, 2 to 3 equivalents of the abovementioned ligands are used per equivalent of palladium metal.

In the process according to the invention, the palladium catalyst is employed in a ratio of from 0.01 to 10 mol %, preferably from 0.05 to 5 and in particular from 0.1 to 3 mol %, based on the compound II.

The process according to the invention can be carried out in a two-phase system consisting of aqueous phase and solid phase, i.e. the catalyst. In this case, the aqueous phase may contain a water-soluble organic solvent in addition to water.

Organic solvents suitable for the process according to the invention are for example ethers, for example dimethoxyethane, diethylene glycol dimethyl ether, tetrahydrofuran, dioxane and tert-butyl methyl ether, hydrocarbons, for example hexane, heptane, cyclohexane, benzene, toluene and xylene, alcohols, for example methanol, ethanol, 1-propanol, 2-propanol, ethylene glycol, 1-butanol, 2-butanol and tert-butanol, ketones, for example acetone, ethyl methyl ketone and isobutyl methyl ketone, and amides, for example dimethylformamide, dimethylacetamide and N-methylpyrrolidone, in each case either on their own or in a mixture.

Preferred solvents are ethers, for example dimethoxyethane and tetrahydrofuran, hydrocarbons, for example cyclohexane, toluene and xylene, and alcohols, for example ethanol, 1-propanol, 2-propanol, 1-butanol and tert-butanol, in each case either on their own or in a mixture.

In a particularly preferred embodiment of the process according to the invention, water, one or more water-insoluble and one or more water-soluble solvents are employed, for example mixtures of water, toluene and ethanol or water, toluene and tetrahydrofuran, preferably in each case in a volume ratio of 1:2:1.

The total amount of solvent is normally from 3000 to 500 and preferably from 2000 to 700 g per mole of the compound II.

Advantageously, the process is carried out by adding the compound II, the boron compound III, the base and the catalytic amount of the palladium catalyst to a mixture of water and one or more inert organic solvents and stirring this mixture at a temperature of from 0 to 150° C., preferably from 30 to 120° C., for a duration of from 1 to 50 hours, preferably from 2 to 24 hours.

The process may be carried out in customary apparatus suitable for such processes.

After the reaction has ended, solid palladium catalyst is removed for example by filtration and the crude product is freed of the solvent or solvents.

When the products are not entirely water-soluble, water-soluble palladium catalysts or complexed ligands are completely removed when separating off the aqueous phase from the crude product.

Subsequent further purification may be carried out using methods known to a person skilled in the art and appropriate for the respective product, for example recrystallization, distillation, sublimation, zone melting, crystallization from the melt or chromatography.

Catalyst which is present as a solid at the end of the reaction is generally easy to remove, to regenerate and to recycle into the process, thus reducing the process costs and avoiding palladium in the waste.

The process according to the invention is suitable for example for preparing:

4'-fluoro-2-nitrobiphenyl
4'-methyl-2-nitrobiphenyl
4'-methoxy-2-nitrobiphenyl
4'-bromo-2-nitrobiphenyl
3'-fluoro-2-nitrobiphenyl
3'-chloro-2-nitrobiphenyl
3'-bromo-2-nitrobiphenyl
3'-methyl-2-nitrobiphenyl
3'-methoxy-2-nitrobiphenyl
4'-phenyl-2-nitrobiphenyl
4'-trifluoromethyl-2-nitrobiphenyl
4'-fluoro-4-nitrobiphenyl 4'-chloro-4-nitrobiphenyl
4'-bromo-4-nitrobiphenyl
4'-methyl-4-nitrobiphenyl
4'-cyano-4-nitrobiphenyl
2-nitrobiphenyl
4-nitrobiphenyl.

The process according to the invention affords the compounds I in high yields and very good purity.

The nitrobiphenyls obtainable by the process according to the invention are useful as precursors for biphenylamines, which in turn are intermediates for fungicidal crop protection agents (cf. EP-A 545 099).

Synthesis of 4'-chloro-2-nitrobiphenyl

EXAMPLE 1

A solution of 9.45 g of 2-nitrochlorobenzene and 10.3 g of 4-chlorophenylboronic acid in 60 ml of tetrahydrofuran was admixed with a solution of 9.6 g of sodium hydroxide in 60 ml of water with stirring and under a nitrogen atmosphere. Subsequently, the mixture was admixed with 70 mg of palladium(II) acetate and 370 mg of triphenylphosphine. The mixture was refluxed (70° C.) with stirring until the 2-nitrochlorobenzene had reacted (about 8 hours). After cooling, the mixture was admixed with 80 ml of water and 80 ml of tert-butyl methyl ether, and the organic phase was separated off. After filtration over 10 g of silica gel and evaporation of the solvent, 13.95 g of the title compound of a purity of 95% (GC) were obtained.

EXAMPLE 2

A solution of 4.7 g of 2-nitrochlorobenzene and 5.6 g of 4-chlorophenylboronic acid in 30 ml of 1,2-dimethoxyethane was admixed with a solution of 8 g of sodium carbonate in 30 ml of water with stirring and under a nitrogen atmosphere. Subsequently, the mixture was admixed with 320 mg of palladium on activated carbon (10% by weight) and 320 mg of triphenylphosphine. The mixture was refluxed with stirring until the 2-nitrochlorobenzene had reacted (about 22 hours). After cooling, the mixture was admixed with 50 ml of water and 50 ml of tert-butyl methyl ether, and the organic phase was separated off. After filtration and evaporation of the solvent, 6.7 g of the title compound of a purity of 92.7% (GC) were obtained.

We claim:

1. A process for preparing 2-nitrobiphenyls of the formula I

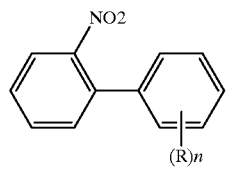

(I)

where R is halogen, R' or OR', where R' is a C-organic radical which may carry groups inert under the reaction conditions, n is 0, 1, 2 or 3, and, in the case of n being 2 or 3, the radicals R are the same or different, which comprises reacting a chloronitrobenzene of the formula II

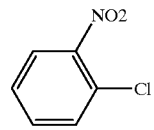

(II)

in the presence of a base and of a palladium catalyst selected from the group consisting of:
 a) palladium triarylphosphine complex having palladium in the oxidation state zero,
 b) palladium salt in the presence of triarylphosphine as complex ligand, and
 c) metallic palladium which is optionally deposited on supports, in the presence of triarylphosphine,
in a solvent with a phenylboronic acid (IIIa)

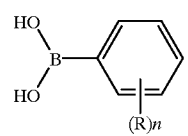

(IIIa)

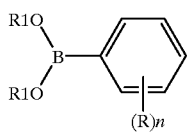

(IIIb)

or an alkyl ester thereof of the formula IIIb where $R^1$ is $C_1$–$C_6$-alkyl, or an anhydride thereof.

2. The process defined in claim 1, wherein the compound IIIa is reacted with the compound II.

3. The process defined in claim 1, wherein R is fluorine, chlorine or a methyl group.

4. The process defined in claim 1, wherein R is chlorine.

5. The process defined in claim 1, wherein the palladium catalyst is tetrakis(triphenylphosphine)palladium.

6. The process defined in claim 1, which is carried out in the presence of the palladium catalyst b).

7. The process defined in claim 1, wherein the palladium catalyst is metallic palladium on activated carbon in the presence of triphenylphosphine whose phenyl groups are substituted with a total of 1 to 3 sulfonate groups.

8. The process defined in claim 2, wherein n is 1 and R is bonded in the 4 position.

9. The process defined in claim 2, wherein from 1 to 1.5 mol of the boronic acid IIIa per mol chloronitrobenzene II are employed.

10. The process defined in claim 2, wherein from 0.01 to 10 mol % of the palladium catalyst per mol chloronitrobenzene II are employed.

11. The process defined in claim 2, which is carried out in a solvent mixture comprising water, a water-soluble solvent and a water-insoluble solvent.

12. The process defined in claim 11, which is carried out in a mixture comprising water, toluene and ethanol.

13. The process defined in claim 11, which is carried out in a mixture comprising water, toluene and tetrahydrofuran.

14. The process defined in claim 2, which is carried out in the presence of a base selected from the group consisting of tertiary amines.

15. The process defined in claim 2, which is carried out in the presence of a base selected from the group consisting of alkali metal hydroxides, alkaline earth metal hydroxides, alkali metal carbonates, alkaline earth metal carbonates, alkali metal bicarbonates, alkali metal acetates, alkaline earth metal acetates, alkali metal alkoxides and alkaline earth metal alkoxides.

16. The process defined in claim 2, which is carried out in the presence of a base selected from the group consisting of alkali metal hydroxides, alkaline earth metal hydroxides, alkali metal carbonates, alkaline earth metal carbonates and alkali metal bicarbonates.

17. The process defined in claim 2, which is carried out in the presence of a base selected from the group consisting of sodium hydroxide, potassium hydroxide, lithium carbonate, sodium carbonate and potassium carbonate.

18. The process defined in claim 1, wherein the base is employed in an amount of from 1 to 5 mol per mol of the boron compound.

19. The process defined in claim 3, wherein the palladium catalyst is tetrakis(triphenylphosphine)palladium.

20. The process defined in claim 3, which is carried out in the presence of the palladium catalyst b).

21. The process defined in claim 3, wherein the palladium catalyst is metallic palladium on activated carbon in the presence of triphenylphosphine whose phenyl groups are substituted with a total of 1 to 3 sulfonate groups.

\* \* \* \* \*